(12) United States Patent
Iyer et al.

(10) Patent No.: US 10,703,682 B2
(45) Date of Patent: Jul. 7, 2020

(54) FERTILIZER PELLETS WITH MICRONIZED SULPHUR

(71) Applicant: SULVARIS INC., Calgary (CA)

(72) Inventors: Satish Iyer, Calgary (CA); Eric Pedersen, Calgary (CA); Richard Knoll, Calgary (CA); Babasola Ajiboye, Calgary (CA)

( * ) Notice: Subject to any disclaimer, the term of this patent is extended or adjusted under 35 U.S.C. 154(b) by 0 days.

(21) Appl. No.: 15/575,231

(22) PCT Filed: May 19, 2016

(86) PCT No.: PCT/CA2016/050569
§ 371 (c)(1),
(2) Date: Nov. 17, 2017

(87) PCT Pub. No.: WO2016/183685
PCT Pub. Date: Nov. 24, 2016

(65) Prior Publication Data
US 2018/0162781 A1    Jun. 14, 2018

Related U.S. Application Data

(60) Provisional application No. 62/163,727, filed on May 19, 2015, provisional application No. 62/240,865, filed on Oct. 13, 2015.

(51) Int. Cl.
| | | |
|---|---|---|
| *C05B 7/00* | (2006.01) | |
| *C05G 1/00* | (2006.01) | |
| *C05B 19/00* | (2006.01) | |
| *C05D 9/02* | (2006.01) | |
| *C05G 3/00* | (2006.01) | |
| *C05D 9/00* | (2006.01) | |
| *C05G 5/12* | (2020.01) | |
| *C01B 17/10* | (2006.01) | |

(52) U.S. Cl.
CPC ................ *C05B 7/00* (2013.01); *C01B 17/10* (2013.01); *C05B 19/00* (2013.01); *C05D 9/00* (2013.01); *C05D 9/02* (2013.01); *C05G 1/00* (2013.01); *C05G 5/12* (2020.02); *C01P 2004/61* (2013.01)

(58) Field of Classification Search
CPC ....................................................... C05D 9/02
See application file for complete search history.

(56) References Cited

U.S. PATENT DOCUMENTS

| | | |
|---|---|---|
| 3,333,939 A | 8/1967 | Davis et al. |
| 4,133,669 A | 1/1979 | Caldwell et al. |
| 4,330,319 A | 5/1982 | Bexton et al. |
| 4,394,150 A | 7/1983 | Garrison et al. |
| 4,569,859 A | 2/1986 | Zaharko |
| 5,571,303 A | 10/1996 | Bexton |
| 5,599,373 A | 2/1997 | Zanuccoli |
| 5,653,782 A | 8/1997 | Stern et al. |
| 5,863,861 A | 1/1999 | Einziger |
| 6,749,659 B1 | 6/2004 | Yu et al. |
| 8,679,446 B2 | 3/2014 | Iyer |
| 8,814,976 B2 | 8/2014 | Pedersen |
| 9,278,858 B2 | 3/2016 | Iyer |
| 10,349,574 B2 * | 7/2019 | Farnworth ............... C05D 9/00 |
| 2002/0151621 A1 * | 10/2002 | Zakiewicz .......... C01B 17/0237 523/207 |
| 2006/0084573 A1 | 4/2006 | Grech et al. |
| 2006/0144108 A1 | 7/2006 | Keenan et al. |
| 2009/0308122 A1 * | 12/2009 | Shah ........................ C05D 9/00 71/27 |
| 2011/0214465 A1 | 9/2011 | Peacock et al. |
| 2011/0302975 A1 | 12/2011 | Antens et al. |
| 2012/0036906 A1 * | 2/2012 | Pedersen ................... C05C 3/00 71/23 |
| 2013/0167604 A1 * | 7/2013 | Abry ...................... C05C 3/005 71/63 |
| 2016/0168040 A1 | 6/2016 | Ferguson et al. |
| 2016/0235093 A1 | 8/2016 | Brion et al. |
| 2017/0096376 A1 | 4/2017 | Farnworth et al. |
| 2017/0327430 A1 | 11/2017 | Allais |

FOREIGN PATENT DOCUMENTS

| | | |
|---|---|---|
| CA | 2952900 | 2/2016 |
| CA | 2971078 | 6/2016 |
| EP | 2583955 | 4/2013 |
| WO | 2014152994 A1 | 9/2014 |
| WO | 2015017329 A2 | 2/2015 |
| WO | 2016183685 | 11/2016 |

\* cited by examiner

*Primary Examiner* — Wayne A Langel
(74) *Attorney, Agent, or Firm* — Bennett Jones LLP

(57) ABSTRACT

Fertilizer pellets may be formed by compressing or compacting a primary fertilizer powder mixed with micronized sulphur.

8 Claims, No Drawings

FERTILIZER PELLETS WITH MICRONIZED SULPHUR

FIELD OF THE INVENTION

The present invention relates to fertilizer compositions and more specifically to fertilizer pellets comprising micronized sulphur.

BACKGROUND

For vigorous growth, plants require primary nutrients, such as carbon, hydrogen, oxygen, nitrogen, phosphorus and potassium, as well as secondary nutrients and micronutrients. Calcium, sulfur and magnesium are considered secondary nutrients and are generally required in smaller quantities than primary nutrients. Micronutrients are required in very small quantities, and include zinc, manganese, iron, copper, molybdenum, boron, chlorine, cobalt and sodium.

Available potassium in the soil is typically augmented with potash (also known as muriate of potash (MOP) or potassium chloride). Available phosphorus in the soil is frequently augmented with solid phosphate fertilizer, typically as monoammonium phosphate (MAP), diammonium phosphate (DAP), or calcium dihydrogen phosphate or monocalcium phosphate ($Ca(H_2PO_4)_2$), known as triple superphosphate (TSP). Available nitrogen may be augmented by urea. These primary nutrient fertilizers are typically known as NPK fertilizers MAP and DAP production methods are well-established and conventionally include the reaction of phosphoric acid ($H_3PO_4$) with ammonia ($NH_3$) in an exothermic reaction.

The reactions may take place in a preneutralizer or a pipe cross reactor (PCR), A preneutralizer is a stirred reactor that produces a slurry of ammonium phosphate. A pipe cross reactor is a pipe-shaped reactor where ammonium phosphate is formed by reacting ammonia and phosphoric acid.

In either case, MAP or DAP or a combination of the two may be produced, depending on the ratio of the ammonia and phosphoric acid reactants. The ammonium phosphate slurry produced in the preneutralizer is supplied to a granulator. Ammonium phosphate formed in a PCR is sprayed into a granulator because the ammonium phosphate produced in the PCR is molten.

Calcium dihydrogen phosphate or monocalcium phosphate ($Ca(H_2PO_4)_2$), known as triple superphosphate (TSP), may be produced by reacting phosphoric acid with phosphate rock.

Generally, solid fertilizer particles are formed by granulation, pelletization or compaction. A granulator is a device for forming granules of fertilizer product. Commonly used granulators are well known in the art and include spray dry granulators, drum granulators, paddle mixers (pug mills) or pan granulators. Preferably, the mixture is pumped and distributed on a rolling bed of material in a drum granulator. Water and/or steam can be fed to the granulator to control the temperature of the granulation process. Granules are then dried and screened, with oversize granules and undersized material (so-called off-spec fines) are recycled back to the granulator. The oversize material may be crushed or ground first before being fed back into the granulator. The undersized and crushed oversized material which is recycled serves a valuable purpose in that it provides seed particles to spur granule formation in the granulator.

In contrast, pelletization is a process by which a powder material is formed into a pellet by compression. As a first step, the fertilizer material may be treated, such as in a crusher, hammer mill or a similar apparatus, to produce a powder comprising relatively uniform small particles, typically less than about 0.70 mm or fine enough to pass through a standard US 25 mesh screen. Secondary and micronutrients in powder form may be incorporated and mixed with the powder as additives at this stage. The powder material may then be mixed and wetted with a small amount of water in preparation for pelletization. Once the mixture has been adjusted to a suitable moisture content, it may be pelletized using a pellet former, such as a mill or press, which uses compression to produce pellets. Suitable pellet mills are well known in the art and may include screw-type extrusion pellet mills.

Compaction is similar to pelletization in that a compressive force is used to produce a pellet, but differs from pelletization in that it uses significantly greater compressive force to cohere the solid material together. Good quality compacted product requires appropriately sized raw materials in powdered form. Since the raw materials are usually available only in a coarse form, they have to be put through a grinder to obtain a fine powder.

However, any grinding or compaction process which processes sulphur has a serious inherent risk of fire or explosion. Elemental sulphur is flammable, and could potentially cause fire or explosion during the production process. The grinding media is bound to generate heat which could ignite the flammable raw material causing explosion.

SUMMARY OF THE INVENTION

In one aspect, the invention comprises a method of producing a fertilizer product, comprising the steps of producing a fertilizer powder suitable for pelletization or compaction, adding micronized sulphur in a desired quantity to produce a mixture, blending the mixture and producing cohered pellets by pelleting the mixture. In one embodiment, the mixture is compacted at high pressure, which may be greater than about 5 Ksi. The resulting compacted pellets are highly dense (greater than about 1.5 g/cm$^3$) and have high crush strength (greater than about 20 lbs. or 9 kg)

In another aspect, the invention may comprise a method of forming a fertilizer pellet, comprising the steps of:
a. Forming a fertilizer powder, and adding micronized sulphur particles and/or micronutrients to the fertilizer powder;
b. Adjusting the moisture content of the fertilizer powder mixture to between about 5% to about 25% water (w/w); and
c. Forming pellets from the fertilizer powder using a compression pelletizing method.

In one embodiment the fertilizer material comprises a phosphate fertilizer compound from a phosphorous source. The phosphorous source may comprise phosphoric acid, and the phosphate fertilizer may comprises MAP and/or DAP.

Undersize and oversize material after the pellet forming step may be recycled to a recycle stream, wherein the recycle stream comprises less than a 300% recycle ratio on a dry weight basis, and preferably less than about 200%, 100%, 50% or 30% recycle ratio on a dry weight basis.

In another aspect, the invention may comprise a pellet formed by compression comprising phosphate fertilizer particles. The pellet may optionally comprise micronized sulphur particles and/or another nutrient or micronutrient.

In one embodiment, the pellet has a crush strength of greater than about 1.4 kg., a resistance-to-attrition (RTA) of greater than about 95%, and/or a dispersibility of more than about 70% through a 12 mesh US Standard screen within 300 seconds of submersion in water.

In another aspect, the invention may comprise a fertilizer pellet comprising a water-soluble NPK fertilizer and micronized sulphur particles formed by compression or compaction, having a crush strength greater than about 1.4 kg and a dispersibility of more than 70% through a 12 mesh US Standard screen within 300 seconds of submersion in water, achieved without requiring a binder, wetting agent, dispersant or disintegrant.

DETAILED DESCRIPTION

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

The present invention relates to fertilizer pellets comprising a primary fertilizer and micronized elemental sulphur, formed by pelletization or by compaction. The primary fertilizer may comprise a water-soluble NPK fertilizer, such as urea, potash, or a phosphate, or combinations thereof. As used herein, a "pellet" is a cohesive or adhesive mass of smaller particles formed by compression, while a "compacted pellet" is a pellet which has been formed by compression in excess of about 5000 psi.

In one embodiment, the invention may relate to compacted fertilizer pellets, comprising any water-soluble NPK fertilizer and micronized sulphur. The fertilizer material is ground prior to sulphur addition, to produce a powder suitable for compaction.

The methods of the present invention are relatively flexible in that it is possible to conveniently incorporate additives to the fertilizer pellets, prior to pelletization or compaction.

Phosphate fertilizer incorporated into the pellets of the present invention may be produced using any known method, and may comprise triple super phosphate (TSP), monoammonium phosphate (MAP) and/or diammonium phosphate (DAP). Generally, a phosphate fertilizer may be produced by the use of phosphoric acid and a source of cations, such as calcium from fluorapatite or hydroxyapatite (phosphate rock), ammonia, sodium, or potassium, to form a fertilizer compound. In one embodiment, MAP or DAP is formed by the reaction between phosphoric acid and ammonia. For example, the methods described in U.S. Pat. No. 7,497,891, the entire contents of which are incorporated herein by reference, where permitted, are particularly suitable. Generally, MAP and/or DAP is produced by a combination of a pre-neutralization reaction and a pipe cross reactor reaction. The formation of ammonium phosphate is initiated in the pre-neutralizer and the reaction proceeds to completion in the pipe-cross reactor. A preneutralizer may be supplied with phosphoric acid and ammonia. The reaction further occurs in a pipe cross reactor (PCR), which is also supplied with phosphoric acid and ammonia. In one embodiment, micronutrients may be supplied to the fertilizer by first dissolving the micronutrients in the acid prior to the pre-neutralizer or the PCR. Different proportions of the product may be produced in the PCR and the preneutralizer, or may be entirely produced in one and not the other.

The preneutralizer is a stirred reactor that produces a slurry of ammonium phosphate. Either MAP or DAP, or a combination of the two, may be produced in the preneutralizer depending on the ratio of ammonia and phosphoric acid. The contact time in the preneutralizer may be 5 to 55 minutes, more particularly, 15 to 45 minutes, and still more particularly, 25 to 35 minutes.

The PCR is a pipe-shaped reactor where ammonium phosphate is formed by reacting ammonia and phosphoric acid. As in the preneutralizer, either MAP or DAP, or a combination of the two, may be produced in the PCR. The heat discharged at the exit to the PCR may be about 600,000 BTU/hr/in$^2$ in one example, as the reaction between ammonia and phosphoric acid is exothermic. The high temperature in the PCR aids in driving the reaction forward at a high rate.

The MAP or DAP produced in the preneutralizer comprises a liquid slurry, while the MAP or DAP produced in the PCR is molten. In either or both cases, the MAP or DAP may be dried, cooled and solidified in a cooling tower or spray dryer, which will produce MAP or DAP particles. The average particle size and morphology will depend greatly on the drying, cooling or solidifying conditions. Conventionally, this fertilizer material would then be granulated in a granulator. However, in embodiments of the present invention, the material is not granulated but rather is pelletized. Granulation is a process by which a particle is formed by cumulative addition of small particles to each other or a seed particle by adhesion to produce a granule. The resulting granules are typically amorphous and may have a wide range of different sizes and morphologies.

In contrast, pelletization is a process by which a powder material is formed into a pellet by compression or by compaction. In embodiments of the present invention, as a first step, the fertilizer material may be treated, such as in a crusher, hammer mill or a similar apparatus, to produce a powder comprising relatively uniform small particles, preferably less than about 1 mm in diameter on average (pass through an 18 mesh screen), more preferably less than about 0.84 mm (fine enough to pass through a 20 mesh screen, and even more preferably less than about 0.70 mm (fine enough to pass through a standard US 25 mesh screen) or smaller.

Micronized elemental sulphur may be added to the mixture prior to or during mixing of the powder. In one embodiment, micronized sulphur particles, such as those described in co-owned U.S. Pat. No. 8,679,446, may be added. The micronized sulphur particles preferably have an average particle diameter of less than 100 microns, or more preferably 30 microns. Most preferably the micronized sulphur particles have an average diameter of 10 microns or smaller. The micronized sulphur product preferably contains sufficient moisture to minimize dust creation, and to minimize flammability, such as between about 2% and 10% by weight. For example, a moisture content of between about 5 to about 7% moisture (by weight) makes it very safe for handling and further processing as it will not dust or easily ignite. It is not desirable to add elemental sulphur at the crushing (powder forming) stage as sulphur dust is an irritant, presents an explosive risk in handling facilities and readily segregates. In one embodiment, sulphur may be added to a concentration of about 5% to 95% or more preferably from about 10% to about 30%, on a dry weight basis.

At this stage, other useful ingredients may be incorporated and mixed with the powder as additives. The additives are preferably either also in powder form or in a form that would quickly breakdown or solubilize upon wetting. Additives may include other primary, secondary or micronutrients (such as, for example, zinc sulphate, zinc oxide, manganese sulphate, manganese oxide, copper sulphate, sodium molybdate and any other micronutrient formulation); fertilizer compounds (such as, for example, potassium chloride, potassium sulphate, magnesium sulphate, etc,); binders (such as, for example, starch, lignosulfonates, molasses, etc.); carbon (such as, for example, activated carbon, carbon matrix, etc.), dispersants (such as, for example, surfactants, etc,), or other materials (such as, for example, humic acid, fulvic acid, etc.) may be added at this stage to a desired proportion. These additives can be added in amounts to achieve any concentration of the additive desired. For example if 1% zinc (by weight) as a micronutrient is desired, one could add 27.8 kg of zinc sulphate monohydrate ($ZnSO_4.H_2O$) per metric tonne, or 14.7 kg of zinc oxide (ZnO) per metric tonne. The additives may be in the form of a powder which rapidly breaks down or is solubilized upon wetting.

In one embodiment, the powder material may then be mixed and wetted with a small amount of water in preparation for pelletization. Preferably, the material comprises about 5 to about 25% water by weight ratio, and more preferably between about 7 to about 20% water by weight. The water content helps the cohesiveness of the resulting pellet.

Once the mixture has been adjusted to a suitable moisture content, it may be pelletized using a pellet former, such as a mill or press, which uses compression to produce pellets. Suitable pellet mills are well known in the art and may include screw-type extrusion pellet mills. With a moisture content greater than about 7% (w/w), the powder material has sufficient cohesion to produce pellets with sufficient integrity for further handling and use, without the use of a binder. Optionally, but not necessarily, a binder may be added.

The pellets formed using the pellet former are then screened to remove pellet fragments or other undersized and oversized material and direct this rejected material into a recycle stream. The recycle stream may be returned to the mixer, or may be used in a different process. In one embodiment, the inventors have found that the pellet forming process results in a surprisingly low recycle rate compared to a granulation process but still produces pellets of commercial quality. In one embodiment, the recycle rate may be less than about 300%, or less than about 200%, or less than about 100%. A recycle rate of 1:1 or 100% means that for every kilogram of on-spec pellets produced, one kilogram of material is recycled. In particularly preferred embodiments, the recycle rate may be under 200%, 100%, 50%, or 40%, or 30%, and may be as low as about 10 to about 15%, This may be contrasted favorably to the prior art granulation methods of producing MAP and DAP, which can have recycle rates in the order of 5:1, or 500%. Such high recycle rates necessitate custom recycle process flows, and add considerably to the capital cost of a manufacturing plant.

On-spec pellets may be dried and screened once again, with the final on spec product cooled and coated, as is well known in the art.

The pellets may have a composition comprising of substantially entirely phosphate (such as either or both of MAP and DAP) or may comprise other primary, secondary or micronutrients.

Pellets of the present invention formed from pellet mills may have a mean particle diameter size that ranges from about 0.4 millimeter to about 15 millimeters. More preferably, the mean particle domain size ranges from about 0.6 millimeter to about 10 millimeters. Still more preferably, the mean particle domain size ranges from about 0.8 millimeter to about 5 millimeters. The pellets formed by the process of the present invention have a Uniformity Index rating in the range of 30 to 95 where the Uniformity Index rating is calculated as the 10th percentile particle size expressed as a percentage of the $95^{th}$ percentile particle size. More preferably, the Uniformity Index rating ranges from 60 to 90.

Pellets of the present invention may take any shape, as determined by the pelleting process. Examples include spheres, cylinders, ellipses, rods, cones, discs, needles and irregular. In one embodiment the pellets are approximately cylindrical and in another embodiment, they are irregularly shaped.

Pellets of the present invention have a crushing strength that may range from about 1.4 kg per pellet to about 8 kg (about 3 pounds to about 18 pounds) per pellet, or higher, which may be achieved without the addition of a binder, although a binder may be optionally added.

Pellets of the present invention may have a resistance to attrition of 95% or greater and more preferably 99% or greater. The test itself involves agitating the particles, typically by tumbling within a drum, vibration, or with jets of gas to simulate a fluidized bed. After a specified time, the material is sieved and the sieved material weighed to measure the proportion of material which has been reduced to below a certain size (referred to as 'fines'). An RTA value of 95% means that after a specified period of time, the pellets retain 95% of their mass. The specifics of the test are defined by various standards as applicable to the purpose in question, such as those defined by ASTM, well known to those skilled in the art.

Pellets of the present invention are dispersible with 25% dispersion or higher and more preferably 70%, and more preferably 90% dispersion or higher through a 12 US standard mesh screen after 300 seconds immersion in water. Such dispersibility may be achieved without the addition of a wetting agent, disintegrant or dispersing agent, although such agents may be optionally added.

In an alternative embodiment, a primary fertilizer such as MAP and/or DAP produced from a reactor is not granulated and is ground in preparation separately using a such as a hammer mill, cage mill, or a roll crusher. This fine powder is then mixed with micronized sulphur.

Moist micronized sulphur powder may then be blended with powdered MAP and/or DAP using any conventional blender like a pin mixer, ribbon blender or screw blender. Any additional nutrients or micronutrients may be added at this point. In one embodiment, no binder is required. The blended powder is then compacted using conventional compaction machinery, such as a double roll compactor for producing granular product. Compaction preferably uses greater than about 5000 psi, 10 Ksi (kilopounds per square inch), 20 or 30 Ksi.

In one embodiment, MAP, DAP or potash having an average particle size of between about 100 microns and 300 microns is particularly suitable for compaction. In one embodiment, an average particle size of about 180 microns is preferred.

In one embodiment, the fertilizer material is mixed with elemental micronized sulphur in a proportion of about 1 to about 30% of sulphur powder by weight of the end product, and preferably in the ratio of about 15% to about 25%.

The resulting compacted pellets preferably have a density greater than about 1.50 $g/cm^3$, preferably greater than about 1.60 $g/cm^3$ and more preferably greater than about 1.80 $g/cm^3$. Certain embodiments may achieve a density of about 2.00 $g/cm^3$.

Compacted test pills may have a crush strength greater than about 20 pounds, preferably greater than about 30 pounds, and more preferably greater than about 50 pounds. Certain embodiments may achieve crush strengths in excess of 100 pounds, or even 200 pounds. Pellet products may have lower crush strengths compared to test pills, which may be used to determine compactibility of different formulations.

The resulting product is water soluble and quickly disintegrates in the soil upon wetting. The micronized sulphur is thus quickly dispersed in the soil and may be oxidized in situ. In one embodiment, as the bulk of the pellet is water soluble, no wetting agent or dispersing agent is required to achieve suitable dispersion, however, optionally a wetting agent, dispersing agent and/or a disintegrant may be added.

EXAMPLES

The following examples are intended solely to illustrate specific embodiments of the invention, and not to limit the claimed invention.

Two batches of a 20 kg (dry weight) mixture was made with the following ingredients:
 i) 17 kg of MAP was ground with a hammer mill until the resulting powder material was fine enough to pass through a US standard 25 mesh screen.
 ii) approximately 3.21 kg of micronized sulfur with an average diameter less than 10 um at 7% moisture content (3.0 kg Sulphur on a dry weight basis); and
 iii) Water to bring the mixture up to about 9% to 10% moisture content (dry weight basis).

The powdered MAP, micronized sulfur and water was then combined and mixed to create the mixture. The resulting mixture was pelletized using a pellet mill manufactured by Amandus Kahl (Germany), model no. 14-175 and a die with 3 mm holes, and a 4:1 or 3:1 compression ratio.

The following parameters were measured:
Micronized sulfur moisture content (prior to mixing with MAP)
Final mixture moisture content
Mass of fines created (an estimate of recycle as no oversize product was produced)
Standard QC tests were conducted after drying for 12 h at 70 C., including % Dispersion through a 12 US standard mesh screen after 300 seconds of being submerged in water, resistance to attrition (RTA), and crushing strength)
Results:

| Batch | Die | Sulfur Moisture Content (%) | Mixture Moisture Content (%) | Crushing Strength (lbs/pellet) | RTA (%) | 300 Second Dispersion (%) | Fines (kg) |
|---|---|---|---|---|---|---|---|
| A | 4 | 5.1 | 9.4 | 17.66 | 99.2 | 78 | 5.2 |
| B | 3C | 6.1 | 10 | 10.72 | 99.4 | 90 | 5.9 |

The dried MAP+S pellets were found to have commercially acceptable quality with high dispersion, high crush strength and good resistance to attrition. The measured recycle rate (fines) ranged from 5.2 to 5.9 kg per 20 kg of powder material (26% to 29.5% on a dry weight basis). The nutrient content of the pellets was about 9% nitrogen, 44% $P_2O_5$, and 15% sulphur.

In the following examples, MAP powder having an average particle size of about 180 microns was blended with micronized sulphur powder having an average particle size of less than 10 microns, and bulk density of 0.507 g/cm3. The blended powder was then compacted in 10 g test pill samples using double roll compaction at a pressure of 10, 20 and 30 Ksi.

In a proportion of 85/15 (MAP/S by weight) the resulting test pills had a density greater than 1.69 g/cm3 and a crush strength of at least 108 pounds, and in excess of 220 pounds for those samples compacted at higher pressure.

| | Pressure (Ksi) | Sample (g) | Pill Area (sq.inch) | Thickness (inch) | Density (g/cc) | Crush Strength (LB) | | |
|---|---|---|---|---|---|---|---|---|
| | | | | | | Fresh | 1.5 hrs@200° F. | 24 hr 70° F. |
| | | | | MAP 85% mix with Sulfur 15% | | | | |
| 1A | 10 | 10 | 1 | 0.360 | 1.69 | 118 | | |
| 1A | 10 | 10 | 1 | 0.364 | 1.68 | 108 | | |
| 1B | 20 | 10 | 1 | 0.337 | 1.81 | >220 | made 5 × 10 mesh sample | |
| 1B | 20 | 10 | 1 | 0.330 | 1.85 | >220 | | |
| 1C | 30 | 10 | 1 | 0.330 | 1.85 | >220 | | |
| 1C | 30 | 10 | 1 | 0.328 | 1.86 | >220 | | |

In a proportion of 75/25 (MAP/S by weight) the resulting test pills had a density greater than 1.72 g/cm³ and a crush strength of at least 62 pounds, and in excess of 115 pounds for those samples compacted at higher pressure.

| | Pressure (Ksi) | Sample (g) | Pill Area (sq.inch) | Thickness (inch) | Density (g/cc) | Crush Strength (LB) | | |
|---|---|---|---|---|---|---|---|---|
| | | | | | | Fresh | 1.5 hrs@200° F. | 24 hr 70° F. |
| | | | | MAP 75% BM with Sulfur 25% | | | | |
| 2A | 10 | 10 | 1 | 0.355 | 1.72 | 62 | | |
| 2A | 10 | 10 | 1 | 0.352 | 1.73 | 64 | | |
| 2B | 20 | 10 | 1 | 0.333 | 1.83 | 115 | | |
| 2B | 20 | 10 | 1 | 0.331 | 1.84 | 125 | | |
| 2C | 30 | 10 | 1 | 0.328 | 1.86 | 128 | | |
| 2C | 30 | 10 | 1 | 0.330 | 1.83 | 136 | | |

Potash granules having a bulk density of 1.054 g/cm³ were also blended with the micronized sulphur described above in a 85/15 ratio. The resulting test pills had a density greater than 1.90 g/cm3 and a crush strength of at least 23 pounds, and in excess of 37 pounds for those samples compacted at higher pressure.

| | Pressure | Sample | Pill Area | Thickness | Density | Crush Strength (LB) | | |
|---|---|---|---|---|---|---|---|---|
| | (Ksi) | (g) | (sq.inch) | (inch) | (g/cc) | Fresh | 1.5 hrs@200° F. | 24 hr 70° F. |
| | | | Potash as received 85% mix with Sulfur 15% | | | | | |
| 3A | 10 | 10 | 1 | 0.319 | 1.91 | 23 | | |
| 3A | 10 | 10 | 1 | 0.321 | 1.90 | 35 | | |
| 3B | 20 | 10 | 1 | 0.308 | 1.98 | 55 | | |
| 3B | 20 | 10 | 1 | 0.310 | 1.97 | 42 | | |
| 3C | 30 | 10 | 1 | 0.306 | 1.99 | 44 | | |
| 3C | 30 | 10 | 1 | 0.306 | 1.99 | 37 | | |

When the potash was milled and screened through a 70 mesh screen prior to mixing and compaction, the crush strength of the resulting pellets increased significantly.

| | Pressure | Sample | Pill Area | Thickness | Density | Crush Strength (LB) | | |
|---|---|---|---|---|---|---|---|---|
| | (Ksi) | (g) | (sq.inch) | (inch) | (g/cc) | Fresh | 1.5 hrs@200° F. | 24 hr 70° F. |
| | | | Potash milled minus 70 mesh 85% mix with Sulfur 15% | | | | | |
| 5A | 10 | 10 | 1 | 0.322 | 1.89 | 70 | | |
| 5A | 10 | 10 | 1 | 0.322 | 1.89 | 78 | | |
| 5B | 20 | 10 | 1 | 0.306 | 1.99 | 130 | made 5 × 10 mesh sample | |
| 5B | 20 | 10 | 1 | 0.307 | 1.99 | 138 | | |
| 5C | 30 | 10 | 1 | 0.303 | 2.01 | 128 | | |
| 5C | 30 | 10 | 1 | 0.303 | 2.01 | 138 | | |
| | | | Potash milled minus 70 mesh 75% mix with Sulfur 25% | | | | | |
| 6A | 10 | 10 | 1 | 0.321 | 1.90 | 56 | | |
| 6A | 10 | 10 | 1 | 0.321 | 1.90 | 56 | | |
| 6B | 20 | 10 | 1 | 0.305 | 2.00 | 93 | | |
| 6B | 20 | 10 | 1 | 0.306 | 1.99 | 83 | | |
| 6C | 30 | 10 | 1 | 0.304 | 2.01 | 70 | | |
| 6C | 30 | 10 | 1 | 0.303 | 2.01 | 86 | | |

DEFINITIONS AND INTERPRETATION

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by the skilled artisan, all numbers, including those expressing quantities of reagents or ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths, or other fractions. As a non-limiting example, each range discussed herein can be readily broken down into a lower third, middle third and upper third.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

What is claimed is:

1. A method of producing a compacted fertilizer pellet, comprising the steps of grinding a water-soluble NPK fertilizer to produce a fertilizer powder having an average particle size between about 100 microns to about 300 microns, adding micronized sulphur in a quantity between about 1% to about 30% dry weight to produce a mixture, blending the mixture and compacting into cohered pellets, using a pressure greater than about 10 Ksi, resulting in pellets having a crush strength greater than about 50 pounds (22.7 kg) per pellet.

2. The method of claim 1 wherein the compaction step uses a pressure greater than about 20 Ksi.

3. A fertilizer pellet produced by compaction using a pressure greater than about 10 Ksi, comprising a water soluble NPK fertilizer having an average particle size between about 100 microns to about 300 microns and micronized elemental sulphur in a quantity between about 1% and 30% by dry weight, the pellet having a density greater than about 1.50 g/ cm$^3$, and a crush strength greater than about 50 pounds (22.7 kg).

4. The fertilizer pellet of claim 3 which comprises about 15% to about 25% micronized sulphur by weight.

5. A method of forming a fertilizer pellet, comprising the steps of:
   (a) forming a fertilizer powder comprising an NPK fertilizer and having an average particle size of less than about 1 mm, and adding micronized sulphur particles in a quantity of between about 10% to about 30% dry weight to the fertilizer powder;
   (b) adjusting the moisture content of the fertilizer powder to between about 5% to about 25% water (w/w);
   (c) forming pellets from the fertilizer powder using a compression pelletizing method; and
   (d) screening undersize and oversize material after the pellet forming step to a recycle stream, wherein the recycle stream comprises less than a 300% recycle ratio on a dry weight basis.

6. The method of claim 5 wherein the NPK fertilizer comprises MAP and/or DAP.

7. The method of claim 5 further comprising the step of adding micronutrients to the fertilizer powder, prior to the pellet forming step.

8. The method of claim 5 wherein the recycle stream comprises less than a 30% recycle ratio on a dry weight basis.

* * * * *